(12) United States Patent
Uttenthal

(10) Patent No.: US 8,088,728 B2
(45) Date of Patent: Jan. 3, 2012

(54) AIRWAY ADMINISTRATION OF TISSUE FACTOR PATHWAY INHIBITOR IN INFLAMMATORY CONDITIONS AFFECTING THE RESPIRATORY TRACT

(75) Inventor: Lars Otto Uttenthal, Salamanca (ES)

(73) Assignee: Drugrecure APS, Horsholm (DK)

( * ) Notice: Subject to any disclaimer, the term of this patent is extended or adjusted under 35 U.S.C. 154(b) by 890 days.

(21) Appl. No.: 11/993,253

(22) PCT Filed: Jun. 23, 2006

(86) PCT No.: PCT/IB2006/002602
§ 371 (c)(1),
(2), (4) Date: Feb. 11, 2008

(87) PCT Pub. No.: WO2006/136962
PCT Pub. Date: Dec. 28, 2006

(65) Prior Publication Data
US 2010/0160218 A1    Jun. 24, 2010

Related U.S. Application Data

(60) Provisional application No. 60/693,968, filed on Jun. 24, 2005.

(51) Int. Cl.
*C07K 14/00* (2006.01)
*A61K 38/00* (2006.01)

(52) U.S. Cl. .............................. 514/2; 530/300; 424/45

(58) Field of Classification Search .................. None
See application file for complete search history.

(56) References Cited

U.S. PATENT DOCUMENTS

| | | | |
|---|---|---|---|
| 4,235,871 A | 11/1980 | Papahadjopoulos et al. | 424/19 |
| 4,501,728 A | 2/1985 | Geho et al. | 424/38 |
| 4,837,028 A | 6/1989 | Allen | 424/450 |
| 4,966,852 A | 10/1990 | Wun et al. | 435/235 |
| 5,106,833 A | 4/1992 | Broze et al. | 514/12 |
| 5,212,091 A | 5/1993 | Diaz-Collier et al. | 435/69.6 |
| 5,312,736 A | 5/1994 | Rasmussen et al. | 435/69.2 |
| 5,378,614 A | 1/1995 | Petersen et al. | 435/69.8 |
| 2003/0139339 A1 | 7/2003 | Creasey | 514/12 |

FOREIGN PATENT DOCUMENTS

| | | |
|---|---|---|
| EP | 1 273 305 | 1/2003 |
| WO | WO 2004/062689 | 7/2004 |
| WO | WO 2006/042017 | 4/2006 |

OTHER PUBLICATIONS

"Ventilation with lower tidal volumes as compared with traditional tidal volumes for acute lung injury and the acute respiratory distress syndrome", N Engl J Med 2000 342:1301-1308.
Amigues et al., "Sirolimus-associated acute respiratory distress syndrome in a renal transplant recipient", Transplant Proc 2005 37:2830-2831.
Bajaj et al., "Inhibitor of the Factor VIIa-Tissue Factor Complex is reduced in patients with disseminated intravascular coagulation but not in patients with severe hepatocellular disease", J Clin Invest 1987 79:1874-1878.
Bellingan, G.J., "The pulmonary physician in critical care-6:the pathogenesis of ALI/ARDS", Thorax 2002 57:540-546.
Idell et al., "Local abnormalities in coagulation and fibrinolytic pathways predispose to alveolar fibrin deposition in the adult respiratory distress syndrome", J Clin Invest 1989 84:695-705.
Kijiyama et al., "Intratracheal gene transfer of tissue factor pathway inhibitor attenuates pulmonary fibrosis", Biochemical and Biophysical Research Communications 2006 339:1113-1119.
Levi et al., "Bronchoalveolar coagulation and fibrinolysis in endotoxemia and pneumonia", Crit Care Med 2003 13(4):S238-S242.
Macintyre, N. R., "Current issues in mechanical ventilation for respiratory failure", Chest 2005 128 (5) :561S-567S.
Sandset et al., "A sensitive assay of extrinsic coagulation pathway inhibitor (EPI) in plasma and plasma fractions", Thrombosis Research 1987 47:389-400.
Szoka, F., Jr., "Comparative properties and methods of preparation of lipid vesicles (LIPOSOMES)", Ann Rev Biophys Bioeng 1980 9:467-508.
Ware et al., "Protein C and thrombomodulin in human acute lung injury", Am J Physiol Lung Cell Mol Physiol 2003 285:L514-L521.
Waterman, M.S., "General methods of sequence comparison", Bulletin of Mathmatical Biology 1984 46(4):473-500.

*Primary Examiner* — Anand Desai
(74) *Attorney, Agent, or Firm* — Licata & Tyrrell P.C.

(57) ABSTRACT

The present invention provides methods for the local treatment of acute and chronic extravascular pulmonary fibrin deposition and/or reducing unwanted effects associated with systemic administration of natural anticoagulants to a subject via airway administration to the subject by intratracheal, intrabronchial or intraalveolar routes of natural anticoagulants or biologically active derivatives thereof.

13 Claims, No Drawings

SEQUENCE LISTING

<160> NUMBER OF SEQ ID NOS: 1

<210> SEQ ID NO 1
<211> LENGTH: 276
<212> TYPE: PRT
<213> ORGANISM: Homo sapiens

<400> SEQUENCE: 1

```
Asp Ser Glu Glu Asp Glu Glu His Thr Ile Ile Thr Asp Thr Glu Leu
1               5                   10                  15

Pro Pro Leu Lys Leu Met His Ser Phe Cys Ala Phe Lys Ala Asp Asp
            20                  25                  30

Gly Pro Cys Lys Ala Ile Met Lys Arg Phe Phe Phe Asn Ile Phe Thr
        35                  40                  45

Arg Gln Cys Glu Glu Phe Ile Tyr Gly Gly Cys Glu Gly Asn Gln Asn
    50                  55                  60

Arg Phe Glu Ser Leu Glu Glu Cys Lys Lys Met Cys Thr Arg Asp Asn
65                  70                  75                  80

Ala Asn Arg Ile Ile Lys Thr Thr Leu Gln Gln Glu Lys Pro Asp Phe
                85                  90                  95

Cys Phe Leu Glu Glu Asp Pro Gly Ile Cys Arg Gly Tyr Ile Thr Arg
            100                 105                 110

Tyr Phe Tyr Asn Asn Gln Thr Lys Gln Cys Glu Arg Phe Lys Tyr Gly
        115                 120                 125

Gly Cys Leu Gly Asn Met Asn Asn Phe Glu Thr Leu Glu Glu Cys Lys
    130                 135                 140

Asn Ile Cys Glu Asp Gly Pro Asn Gly Phe Gln Val Asp Asn Tyr Gly
145                 150                 155                 160

Thr Gln Leu Asn Ala Val Asn Asn Ser Leu Thr Pro Gln Ser Thr Lys
                165                 170                 175

Val Pro Ser Leu Phe Glu Phe His Gly Pro Ser Trp Cys Leu Thr Pro
            180                 185                 190

Ala Asp Arg Gly Leu Cys Arg Ala Asn Glu Asn Arg Phe Tyr Tyr Asn
        195                 200                 205

Ser Val Ile Gly Lys Cys Arg Pro Phe Lys Tyr Ser Gly Cys Gly Gly
    210                 215                 220

Asn Glu Asn Asn Phe Thr Ser Lys Gln Glu Cys Leu Arg Ala Cys Lys
225                 230                 235                 240

Lys Gly Phe Ile Gln Arg Ile Ser Lys Gly Gly Leu Ile Lys Thr Lys
                245                 250                 255

Arg Lys Arg Lys Lys Gln Arg Val Lys Ile Ala Tyr Glu Glu Ile Phe
            260                 265                 270

Val Lys Asn Met
            275
```

AIRWAY ADMINISTRATION OF TISSUE FACTOR PATHWAY INHIBITOR IN INFLAMMATORY CONDITIONS AFFECTING THE RESPIRATORY TRACT

This patent application is the National Stage of International Application No. PCT/IB2006/002602, filed Jun. 23, 2006, which claims the benefit of priority from U.S. Provisional Patent Application Ser. No. 60/693,968, filed Jun. 24, 2005, teachings of each of which are herein incorporated by reference in their entirety.

All patent and non-patent references cited in the application, or in the present application, are also hereby incorporated by reference in their entirety.

FIELD OF INVENTION

The present invention provides methods to arrest acute, recurrent and chronic fibrin deposition in the airspaces of the respiratory tract, in particular the alveoli and/or bronchioli, in any disease associated with such deposition in children and adults. These diseases include inflammatory lung diseases such as acute lung injury (ALI), which may be related to direct or indirect pulmonary trauma, e.g. following ventilator therapy (Ventilatory Induced Lung Injury (VILI)), inflammatory conditions like autoimmune diseases, pancreatitis, aspiration pneumonitis, inhalation of toxic fumes, acute respiratory distress syndrome (ARDS), which is a more severe manifestation of ALI, infections such as sepsis, severe sepsis and septic shock; pneumonia of whatever cause; acute and chronic bronchoalveolar diseases, fibrosing alveolitis, bronchiolitis, cystic fibrosis and also diseases with severe airway hyperreactivity, e.g. bronchial asthma and drug induced lung insufficiency, e.g. following chemotherapy like bleomycin. In the methods of the present invention, anticoagulants such as tissue factor pathway inhibitor, whether these agents are derived from plasma or prepared by recombinant DNA technology, are administered intratracheally, intrabronchially, or to the alveolar space via airway administration. These methods are useful in clinical medicine, especially critical or intensive care medicine and respiratory medicine.

BACKGROUND OF INVENTION

The deposition of fibrin in the airspaces of the respiratory tract, particularly the alveolar and bronchiolar airspaces, is a frequent complication of systemic inflammatory conditions such as those resulting from trauma, sepsis, severe sepsis and septic shock, drug induced ALI, ARDS or pneumonitis (e.g. due to metothrexate, bleomycin or sirolimus) (Amigues L, Klouche K, Massanet P, Gaillard N, Garrigue V, Beraud J J, Mourad G. Sirolimus-associated acute respiratory distress syndrome in a renal transplant recipient. Transplant Proc. 2005; 37:2830-1.) and ventilator-induced lung injury (VILI) (MacIntyre N R. Current issues in mechanical ventilation for respiratory failure. Chest. 2005; 128:561 S-567S) and lung injury secondary to mechanical ventilation (VILI (The Acute Respiratory Distress Syndrome Network: Ventilation with lower tidal volumes as compared with traditional tidal volumes for acute lung injury and the acute respiratory distress syndrome. N Engl J. Med. 2000; 342:1301-1308.

These conditions lead to a systemic activation of coagulation, ultimately resulting in the deposition of fibrin in the intravascular and extravascular spaces, i.e. in the alveolar and bronchial compartments. At the same time, the inflammatory activation causes the release of pro-inflammatory cytokines such as tumor necrosis factor alpha (TNF-α), interleukin 1-beta (IL-1β), interleukin 6 (IL-6) and interleukin 8 (IL-8) from activated inflammatory cells. Intravascular fibrin deposition and the release of pro-inflammatory cytokines in the airspaces of the lungs cause a tissue injury characterized by an increased permeability of the alveolar-capillary membrane with diffuse alveolar damage and the accumulation in the alveoli of edema fluid rich in plasma proteins, including the components of the blood coagulation system, and a reduction in surfactant production. As a result, a fibrin-rich hyaline membrane is formed in the alveolar ducts and airspaces. In a later phase, a massive infiltration of neutrophils and other inflammatory cells occurs, followed by organization of the exudates and fibrosis. This pathologic sequence has been described and reviewed by Bellingan G J, 2002: "The pathogenesis of ALI/ARDS", Thorax 57:540-546. The clinical conditions corresponding to this pathology are called ALI or ARDS, differing only in that ARDS is more severe and characterized by greater hypoxemia such that the ratio of arterial $P_{O2}$ to inspired oxygen fraction $(Pa_{O2}/FI_{O2}) \leq 200$ mmHg. ALI and ARDS occur as part of the systemic inflammatory response syndrome (SIRS), which can be due infective or non-infective causes such as pancreatitis or direct or indirect pulmonary trauma; when the cause of SIRS is infective, it is called sepsis, which, when associated with organ dysfunction, is defined as severe sepsis, and when associated with significant hypotension, as septic shock.

A similar sequence of pathological events occurs in pneumonias due to a variety of causes, including viral, bacterial and fungal agents, e.g. *Pneumocystis carinii* (PCP) pneumonia, bronchiolitis (e.g. secondary to viral pneumonitis and/or pulmonary graft-versus-host disease (GVHD)), leading also to alveolar exudates and fibrin deposition in those regions of the lung affected by the inflammatory process.

It has been pointed out (e.g. by Levi M et al., 2003: "Bronchoalveolar coagulation and fibrinolysis in endotoxemia and pneumonia", Crit. Care Med 31:S238-S242) that the lung is particularly susceptible to fibrin deposition in sepsis, showing this phenomenon to a greater degree than other organs. The extensive local fibrin deposition suggests that local activation of coagulation or perturbation of local physiologic regulatory systems may be involved. In the bronchoalveolar compartment, tissue factor (TF), expressed locally on alveolar macrophage cells and on the epithelium, seems to have a pivotal role in the initiation of coagulation, while physiologic anticoagulation due to antithrombin and the protein C system is dysfunctional. It has been documented that the protein C system is markedly disrupted in patients with ALI/ARDS from both septic and non-septic causes and there is evidence of both circulatory and intra-alveolar derangements in the protein C pathway in ALI/ARDS (Ware L B et al., 2003: "Protein C and thrombomodulin in human acute lung injury", Am J Physiol Lung Cell Mol Physiol 285:L514-L521).

At the same time, there is a marked depression of local fibrinolysis, i.e. coagulation is locally upregulated in the injured lung, while fibrinolytic activity is markedly depressed.

SUMMARY OF INVENTION

The aim of the present invention is to improve the treatment of ALI, ARDS, pneumonia and inflammatory pulmonary diseases by addressing the local pulmonary activation of the coagulation system and the local deficiency of anticoagulatory mechanisms, by applying the relevant anticoagulants, or agents capable of blocking the local initiation of coagulation, by local administration into the airways. In this way a high local concentration of these agents can be achieved in the affected airways, so that extravascular fibrin deposition can be more effectively inhibited than by the systemic (intravenous) administration of the same agents, but avoiding or reducing systemic adverse effects. The airway administration of these agents can be given alone or as a supplement to intravenous administration of the same or other agents. Because of the "cross-talk" between coagulation and inflammation, the airway administration of these agents is also expected to modulate local pulmonary inflammation, by reducing local thrombin activation and in certain cases also by direct anti-inflammatory action.

An aspect of the present invention relates to a method for reducing extravascular fibrin deposition in the airways, especially in the alveolar or bronchoalveolar spaces, in human subjects with inflammatory and/or infective pulmonary conditions that lead to such fibrin deposition, the method comprising the administration via the airway of anticoagulants, whether purified from plasma or obtained by recombinant DNA technology.

DETAILED DESCRIPTION OF THE INVENTION

The present invention relates to the airway administration, by any appropriate method including, but not limited to, intratracheal, intrabronchial or intraalveolar administration, to a human subject inclusive, of both adults and children, of purified or concentrated natural human tissue factor pathway inhibitor (TFPI), or derivatives thereof, however prepared, to prevent or reduce extravascular fibrin deposition in the airways, especially the alveolar or bronchoalveolar airspaces. Such fibrin deposition may result from an acute condition, a recurrent condition or a chronic condition and may be due to a variety of causes, including but not limited to trauma, direct or indirect, inflammation or infection, due to drug induced fibrin deposition in airways and lung interstitium, congentinal diseases like cystic fibrosis, or due to a combination of such possible causes. For example, it is believed that the methods of the present invention will be useful in treating the alveolar fibrin deposition characteristic of ALI or ARDS arising in a large proportion of patients with sepsis of varying degrees, in patients with severe pneumonias, bronchiolitis obliterans and in fibrosing alveolitis.

Definitions

Affinity: the strength of binding between receptors and their ligands, for example between an antibody and its antigen.

Amino Acid Residue: That part of the amino acid which is present in the polypeptide chain in which the amino acid is linked to other amino acids by peptide (amide) bonds. The amino acid residues described herein are preferably in the "L" isomeric form. However, the amino acid encompasses every amino acid such as L-amino acid, D-amino acid, alpha-amino acid, beta-amino acid, gamma-amino acid, natural amino acid and synthetic amino acid or the like, as long as the desired functional property is retained by the polypeptide. Further included are natural or synthetic amino acids which have been modified. $NH_2$ refers to the free amino group present at the amino terminus of a polypeptide. COOH refers to the free carboxy group present at the carboxy terminus of a polypeptide. Standard polypeptide abbreviations for amino acid residues are used herein.

It should be noted that all amino acid residue sequences represented herein by formulae have a left-to-right orientation in the conventional direction of amino terminus to carboxy terminus. Furthermore, it should be noted that a dash at the beginning or end of an amino acid residue sequence indicates a peptide bond to a further sequence of one or more amino acid residues or a covalent bond to an amino-terminal group such as $NH_2$ or acetyl or to a carboxy-terminal group such as COOH.

Modified amino acid: an amino acid wherein an arbitrary group thereof is chemically modified. In particular, a modified amino acid chemically modified at the alpha carbon atom in an alpha-amino acid is preferable.

Polypeptide: The phrase polypeptide refers to a molecule comprising amino acid residues which do not contain linkages other than amide linkages between adjacent amino acid residues. The phrase peptide is used accordingly.

TFPI Molecule

The present invention relates to the use of TFPI molecule(s) in the manufacture of a medicament for the local treatment of acute and extravascular pulmonary fibrin deposition. The term "TFPI molecule" is used herein to refer to any molecule capable of binding to and inhibiting directly or indirectly the coagulation factors VIIa, Xa and/or tissue factor (TF). Normally, TFPI exists in plasma both as a full-length molecule and as variably carboxy-terminal truncated forms. TFPI also circulates in complex with plasma lipoproteins.

Methods for assaying the functional activity of the TFPI molecules for use in the present invention include those described by Bajaj et al., J Clin Invest 79, p 1874-1878, 1987; Sandset et al., Thromb Res 47, p 389-400, 1987.

It is to be understood that the activity of the TFPI molecules for use in the present invention can be less potent or more potent than native TFPI.

TFPI is an endogenous serine protease inhibitor, synthesized and secreted by endothelia) cells, which is also known as lipoprotein-associated coagulation inhibitor (LACI), tissue factor inhibiter (TFI), and intrinsic pathway Inhibitor (EPI). TFPI has anticoagulant properties. Human TFPI is a polypeptide of 276 amino acids, which contains 18 cysteine residues and forms 9 disulfide bridges when correctly folded. The primary sequence contains three N-linked consensus glycosylation sites (AsnX-Ser/Thr). The asparagine residues of the glycosylation sites are located at positions 145, 195 and 256. The TFPI polypeptide contains three Kunitz-type enzyme inhibitor domains.

The present invention further includes the use of recombinant or synthetically or transgenically produced human TFPI peptides. Thus in one embodiment, the TFPI molecule is a homologue of TFPI.

The human tissue factor pathway inhibitor that is intended to be administered according to the present invention comprises naturally occurring human tissue factor pathway inhibitor, or biologically active analogues of the same, whether prepared from plasma or recombinantly or transgenically or synthetically produced. Recombinant tissue factor pathway inhibitor may incorporate modifications (e.g. amino acid substitutions and/or deletions and/or additions of heterologous amino acid sequences), which may result in analogues with enhanced biologic activity. For example, the TFPI can be produced using eukaryotic cell culture systems (e.g. human kidney 293, HEPG-2, SKHep, LLC-MK2, CHO or AV12 cells), transgenic animals, transgenic plants, or in vitro systems. In these systems, the protein can be produced as an inactive precursor, which, after purification, is proteolytically cleaved and formulated for administration or in its mature form.

Details of producing, purifying, activating, and formulating TFPI are known in the art and are described, for example, in U.S. Pat. No. 5,212,091, which is incorporated by reference herein in its entirety. Also, TFPI genes and plasmids that can be used in these methods are described in U.S. Pat. No. 4,966,852, which is also incorporated by reference herein.

Tissue factor pathway inhibitor can also be obtained from commercial sources. For instance, a specific example of an TFPI that can be used in the invention is produced by Chiron Corporation, under the name of Tifacogin™ (recombinant tissue factor pathway inhibitor).

In one preferred embodiment of the present invention, the TFPI molecule is an TFPI analogue. An "TFPI analogue" is defined as a molecule having one or more (such as 20 or fewer, for example 17 or fewer, such as 15 or fewer, for example 13 or fewer, such as 11 or fewer, for example 9 or fewer, such as 7 or fewer, for example 5 or fewer, such as 3 or fewer, for example 2 or fewer, such as 1 or fewer) amino acid substitutions, deletions, inversions, or additions relative to TFPI and may include D-amino acid forms.

TFPI analogues also have been described in U.S. Pat. No. 5,106,833, where analogues and fragments are disclosed, U.S. Pat. Nos. 5,312,736 and 5,378,614, and WO 2004/062689, which herby are incorporated by reference herein in their entirety.

Preferred TFPI molecules used in the present invention also include analogues of TFPI in which one or more amino acids which are not present in the original sequence are added or deleted, and derivatives thereof.

In one embodiment of the present invention the TFPI analogue exhibits an enhanced anticoagulant activity compared with the wild-type protein. In a preferred embodiment the analogue has a higher binding affinity for its binding partners, such as for example factor VIIa, Xa and TF, than the wild-type protein. In a further embodiment the modifications result in a stabilization of the TFPI analogue. TFPI analogues can be used according to the present invention alone or in combination with other TFPI analogues and or homologues and/or derivatives and/or conjugates. For example a TFPI analogue with a higher binding affinity for factor VIIa, Xa and/or TF can be used in combination with a stabilized TFPI homologue.

In another preferred embodiment of the present invention, the TFPI molecule is an TFPI derivative. A "TFPI derivative" is defined as a molecule having the amino acid sequence of TFPI or of an TFPI analogue, but additionally comprises chemical modification of one or more of its amino acid side groups, alpha-carbon atoms, terminal amino group, or terminal carboxylic acid group. A chemical modification includes, but is not limited to, adding chemical moieties, creating new bonds, and removing chemical moieties. Modifications at amino acid side groups include, without limitation, acylation of lysine epsilon-amino groups, N-alkylation of arginine, histidine, or lysine, alkylation of glutamic or aspartic carboxylic acid groups, and deamidation of glutamine or asparagine. Modifications of the terminal amino include, without limitation, the des-amino, N-lower alkyl, N-di-lower alkyl, and N-acyl modifications. Modifications of the terminal carboxy group include, without limitation, the amide, lower alkyl amide, dialkyl amide, and lower alkyl ester modifications. Lower alkyl is C1-C4 alkyl. Furthermore, one or more side groups, or terminal groups, may be protected by protective groups known to the ordinarily-skilled protein chemist. The alpha-carbon of an amino acid may be mono- or dimethylated.

Homologues of TFPI Molecules

A homologue of one or more of the sequences specified herein may vary in one or more amino acids as compared to the sequences defined, but is capable of performing the same function, i.e. a homologue may be envisaged as a functional equivalent of a predetermined sequence.

Thus, in one preferred embodiment of the present invention, the TFPI molecule is a homologue of any of the molecules disclosed herein, such as a homolog of any of the molecules selected from the group consisting of:
TFPI
Tifacogin Thus, in one preferred embodiment of the present invention, the TFPI molecule is a peptide containing one or more amino acid substitutions, inversion, additions and/or deletions, compared with any of the molecules disclosed herein, such as a molecule selected from the group consisting of:
TFPI
Tifacogin In one embodiment, the number of substitutions, deletions, or additions is 20 amino acids or less, such as 15 amino acids or less, for example 10 amino acids or less, such as 9 amino acids or less, for example 8 amino acids or less, such as 7 amino acids or less, for example 6 amino acids or less, such as 5 amino acids or less, for example 4 amino acids or less, such as 3 amino acids or less, for example 2 amino acids or less (such as 1), or any integer in between these amounts. In one aspect of the invention, the substitutions include one or more conservative substitutions, such as 20 or fewer conservative substitutions, for example 18 or fewer, such as 16 or fewer, for example 14 or fewer, such as 12 or fewer, for example 10 or fewer, such as 8 or fewer, for example 6 or fewer, such as 4 or fewer, for example 3 or fewer, such as 2 or fewer conservative substitutions. A "conservative" substitution denotes the replacement of an amino acid residue by another, related amino acid residue belonging to the same group of amino acids, such as those with a hydrophobic side chain, those with an aromatic side chain, those with a basic side-chain, those with an acidic side chain, those with a hydroxyl side chain and those with a non-ionized polar side chain. Examples of conservative substitution include the substitution of one hydrophobic residue, such as isoleucine, valine, leucine or methionine for another, or the substitution of one basic residue for another, such as the substitution of arginine for lysine, or the substitution of one acidic residue for another, such as glutamic acid for aspartic acid, or the substitution of one non-ionized polar residue for another, such as the substitution of glutamine for asparagine, and the like. The following table lists illustrative, but non-limiting, conservative amino acid substitutions.

| Original residue | Exemplary substitutions |
|---|---|
| Ala | Ser, Thr, Val, Gly |
| Arg | Lys |
| Asn | His, Ser |
| Asp | Glu, Asn |
| Cys | Ser |
| Gln | Asn, His |
| Glu | Asp, Glu |
| Gly | Ala, Ser |
| His | Asn, Gln |
| Ile | Leu, Val, Thr |
| Leu | Ile, Val |
| Lys | Arg, Gln, Glu, Thr |
| Met | Leu, Ile, Val |
| Phe | Leu, Tyr |
| Ser | Thr, Ala, Asn |
| Thr | Ser, Ala |
| Trp | Arg, Ser |
| Tyr | Phe |
| Val | Ile, Leu, Ala |
| Pro | Ala |

Other TFPI homologues suitable for the uses and methods of the present invention are peptide sequences having greater than 50 percent sequence identity, and preferably greater than 90 percent sequence identity (such as greater than 91% sequence identity, for example greater than 92% sequence identity, such as greater than 93% sequence identity, for example greater than 94% sequence identity, such as greater than 95% sequence identity, for example greater than 96% sequence identity, such as greater than 97% sequence identity, for example greater than 98% sequence identity, such as greater than 99% sequence identity, for example greater than 99.5% sequence identity), to any of the molecules disclosed herein, such as a molecule selected from the group consisting of:

TFPI

Tifacogin

As used herein, sequence identity refers to a comparison made between two molecules using standard algorithms well known in the art. The preferred algorithm for calculating sequence identity for the present invention is the Smith-Waterman algorithm, where the reference sequence is used to define the percentage identity of polypeptide homologs over its length. The choice of parameter values for matches, mismatches, and inserts or deletions is arbitrary, although some parameter values have been found to yield more biologically realistic results than others. One preferred set of parameter values for the Smith-Waterman algorithm is set forth in the "maximum similarity segments" approach, which uses values of 1 for a matched residue and −⅓ for a mismatched residue (a residue being either a single nucleotide or single amino acid) (Waterman, Bull. Math. Biol. 46, 473-500 (1984)). Insertions and deletions (indels), x, are weighted as $$x_k = 1 + k/3,$$

where k is the number of residues in a given insert or deletion (Id.).

For instance, a sequence that is identical to a 42 amino acid residue sequence, except for 18 amino acid substitutions and an insertion of 3 amino acids, would have a percent identity given by:

$$[(1 \times 42 \text{ matches}) - (\tfrac{1}{3} \times 18 \text{ mismatches}) - (1 + \tfrac{3}{3} \text{ indels})]/42 = 81\% \text{ identity}$$

In one preferred embodiment of the present invention, truncations at the end of the molecule are not taken into account when calculating sequence identity (i.e., if one molecule is longer than the other, only the overlapping lengths of the molecules are used in the sequence identity analysis); in another preferred embodiment of the present invention, truncations are counted as deletions.

A TFPI homologue may include D-amino acid forms and may be a molecule having one or more amino acid substitutions, deletions, inversions, or additions relative to any of the molecules disclosed herein, such as a molecule selected from the group consisting of:

TFPI

Tifacogin

In one preferred embodiment of the present invention, the TFPI molecule is a peptide containing one or more amino acid substitutions, inversion, additions or deletions, compared with TFPI. In one embodiment, the number of substitutions, deletions, or additions is 20 amino acids or less, such as 15 amino acids or less, for example 10 amino acids or less, such as 9 amino acids or less, for example 8 amino acids or less such as 7 amino acids or less, for example 6 amino acids or less, such as 5 amino acids or less, for example 4 amino acids or less, such as 3 amino acids or less, for example 2 amino acids or less (such as 1), or any integer in between these amounts. In one aspect of the invention, the substitutions include one or more conservative substitutions. Examples of suitable conservative substitutions are given above.

Other TFPI homologues suitable for the uses and methods of the present invention are peptide sequences derived from protein C sequences having greater than 50 percent sequence identity, and preferably greater than 90 percent sequence identity (such as greater than 91% sequence identity, for example greater than 92% sequence identity, such as greater than 93% sequence identity, for example greater than 94% sequence identity, such as greater than 95% sequence identity, for example greater than 96% sequence identity, such as greater than 97% sequence identity, for example greater than 98% sequence identity, such as greater than 99% sequence identity, for example greater than 99.5% sequence identity), to (1) SEQ ID NO:1 and/or (2) to truncated sequences thereof. As used herein, sequence identity refers to a comparison made between two molecules using standard algorithms well known in the art. The preferred algorithm for calculating sequence identity for the present invention is the Smith-Waterman algorithm, as described above.

An TFPI homologue may also be a molecule having one or more amino acid substitutions, deletions, inversions, or additions relative to human TFPI and may include D-amino acid forms.

In another embodiment of the present invention, said homologue of any of the predetermined sequences herein, such as SEQ ID NO: 1 may be defined as:
i) homologues comprising an amino acid sequence capable of binding selectively to the coagulation factors VIIa, Xa and/or TF, and/or
ii) homologues having a substantially similar or higher binding affinity to the coagulation factors VIIa, Xa and/or TF than human TFPI, and/or
iii) homologues having substantially similar, higher or lower half life after deposition in the airways Chemically Derivatized TFPI Molecules It is further understood that TFPI molecules suitable for use in the present invention may be chemically derivatized or altered, for example, peptides with non-natural amino acid residues (e.g., taurine residue, beta- and gamma-amino acid residues and D-amino acid residues), C-terminal functional group modifications, such as amides, esters, and C-terminal ketone modifications and N-terminal functional group modifications, such as acylated amines, Schiff bases, or cyclization, such as found, for example, in the amino acid pyroglutamic acid.

TFPI Molecule Conjugates

The TFPI molecules of the present invention may also be modified with non-polypeptide moieties to yield TFPI compounds that have an increased resistance to inactivation by e.g. proteolytic degradation.

Thus, in one embodiment of the present invention, the TFPI molecule used is an N-glycosylated TFPI peptide or an analogue thereof.

In another embodiment of the present invention, the TFPI molecule is an O-glycosylated TFPI peptide or an analogue thereof.

In another embodiment of the present invention, the TFPI molecule used is an TFPI polypetide or an analogue thereof further containing and N-linked or O-linked fatty acid.

TFPI Fragments

In one embodiment the TFPI molecule can be a TFPI fragment. A fragment is a portion of TFPI, TFPI homologue or TFPI derivative. Examples of fragments include Kunitz domains 1, 2 or 3, Kunitz domains 1 and 2 or 2 and 3, or deletions of the N-terminus or the C-terminus or both. Fragments of TFPI comprise at least 20 consecutive amino acids from SEQ ID NO: 1. For example a fragment can be 20 amino acids or more, such as 25 amino acids or more, for example 30 amino acids or more, such as 50 amino acids or more, for example 100 amino acids or more, such as 150 amino acids or more, for example 200 amino acids or more, such as 250 amino acids or more, for example 275 amino acids in length or any integer in between these amounts.

Intratracheal, Intrabronchial or Intraalveolar Administration

Methods of administration include, but are not limited to, spraying, lavage, inhalation, flushing or installation, using as fluid a physiologically acceptable composition in which the blood coagulation factor or factors have been dissolved. When used herein the terms "intratracheal, intrabronchial or intraalveolar administration" include all forms of such administration whereby the coagulation factor is applied into the trachea; the bronchi or the alveoli, respectively, whether by the instillation of a solution of the factor, by applying the factor in a powder form, or by allowing the factor to reach the relevant part of the airway by inhalation of the factor as an aerosolized or nebulized solution or powder or gel, with or without added stabilizers or other excipients.

In another embodiment, intratracheal, intrabronchial or intraalveolar administration does not include inhalation of the product but the instillation or application of a solution of the factor or a powder or a gel containing the factor into the trachea or lower airways.

Methods of intrabronchial/alveolar administration include, but are not limited to, bronchoalveolar lavage (BAL) administration according to methods well known to those skilled in the art, using as a lavage fluid a physiologically acceptable composition in which the TFPI and/or a TFPI homolog and/or derivative and/or conjugate has been dissolved, or indeed by any other effective form of intrabronchial administration including the use of nebulized powders containing the anticoagulant in dry form, with or without excipients, or the direct application of the anticoagulant in solution or powder or gel form during bronchoscopy. Methods of intratracheal administration include, but are not limited to, blind tracheal washing with a similar solution of dissolved tissue factor pathway inhibitor, or the inhalation of nebulized aerosolized fluid droplets containing the dissolved tissue factor pathway inhibitor obtained by use of any nebulizing apparatus adequate for this purpose.

The present invention provides a useful new addition to the methods of treating ALI, ARDS, pneumonia and other conditions associated with bronchoalveolar fibrin deposition. Furthermore, the administration of the anticoagulants via the airway is expected to avoid the unwanted hemorrhagic adverse effects of systemic administration of anticoagulants such as TFPI, whose intravenous use is associated with a significant incidence of internal hemorrhage including cerebral hemorrhage. At the same time, the application of the anticoagulants via the airway is expected to potentiate their effect on extravascular fibrin deposition in the lungs when compared with their systemic administration. It is expected that the total dosage of an anticoagulant and anti-inflammatory agent such as TFPI may be used alone locally within the airspaces or may be divided between the conventional intravenous route and the airway route of the present invention to obtain the optimal balance between the systemic and local pulmonary effects of the treatment, and a reduced incidence of drug adverse effect, for example in patients with severe sepsis, septic shock and ARDS. Furthermore, the time interval ("window of opportunity") during which the intravenous use of TFPI is likely to be beneficial is limited. A longer time interval of drug response may be expected when the agent is used in the post-septic phase or even in the late ARDS phase dominated by alveolar fibrin deposition, e.g. as seen in ALI and ARDS.

A preferred embodiment of the present invention comprises local intrabronchial administration to human patients with ARDS of TFPI by means of bronchoalveolar lavage with lavage fluid (e.g. 25 ml to 100 ml of isotonic saline) in which a suitable dose (e.g. 2 mg to 5 mg or more) of TFPI has been dissolved. This administration is repeated at intervals during one or more days depending on the duration of either early or late phases of ALI or ARDS. As supplementary or combinatorial treatments in patients fulfilling the indications for intravenous administration of TFPI, TFPI can also be given by intravenous infusion.

Other preferred methods of administration may include using the following devices:
1. Pressurized nebulizers using compressed air/oxygen mixture
2. Ultrasonic nebulizers
3. Electronic micropump nebulizers (e.g. Aeroneb Professional Nebulizer)
4. Metered dose inhaler (MDI)
5. Dry powder inhaler systems (DPI), The aerosol may be delivered by via a) facemasks or b) via endotracheal tubes in intubated patients during mechanical ventilation (device 1, 2 and 3). The devices 4 and 5 can also be used by the patient without assistance provided that the patient is able to self-activate the aerosol device.

Preferred concentrations for a solution comprising TFPI and/or homologues and/or derivatives of TFPI are in the range of 0.1 µg to 10000 µg active ingredient per ml solution. Using monomeric forms of the compounds, the suitable concentrations are often in the range of from 0.1 µg to 5000 µg per ml solution, such as in the range of from about 0.1 µg to 3000 µg per ml solution, and especially in the range of from about 0.1 µg to 1000 µg per ml solution, such as in the range of from about 0.1 µg to 250 µg per ml solution. A preferred concentration would be from about 0.1 to about 5.0 mg, preferably from about 0.3 mg to about 3.0 mg, such as from about 0.5 to about 1.5 mg and especially in the range from 0.8 to 1.0 mg per ml solution. Using multimeric forms of the compounds, the suitable concentrations are often in the range of from 0.1 µg to 1000 µg per ml solution, such as in the range of from about 0.1 µg to 750 µg per ml solution, and especially in the range of from about 0.1 µg to 500 µg per ml solution, such as in the range of from about 0.1 µg to 250 µg per ml solution. A preferred concentration would be from about 0.1 to about 5.0 mg, preferably from about 0.3 mg to about 3.0 mg, such as from about 0.5 to about 1.5 mg and especially in the range from 0.8 to 1.0 mg per ml solution.

Indications

One aspect of the present invention relates to a method of treating or preventing extravascular fibrin deposition in the airways. Thus, the present invention relates to the treatment of individuals suffering from, or at risk of suffering from, extravascular fibrin depositions caused by an inflammatory lung disease.

In a preferred aspect the inflammatory lung disease is selected from the group consisting of:
ALI
ARDS
pneumonia
acute bronchoalveolar disease
chronic bronchoalveolar disease
fibrosing alveolitis or
bronchial asthma
Alveolitis
Bronchiolitis
Bronchiolitis obliterans-organizing pneumonia (BOPA)
Graft-versus-host disease (GVHD)

*Pneumocystis carinii* pneumonia (PCP)
Pneumonitis, e.g. aspiration pneumonitis
Drug-Induced pneumonitis (e.g. due to methothrexate, bleomycin or sirolimus)
Fibrosing alveolitis, acute or chronic
Cystic fibrosis
Idiopathic pulmonary fibrosis In another embodiment, the inflammatory lung disease is related to a condition selected from the group consisting of:
direct or indirect pulmonary trauma
pancreatitis
aspiration pneumonitis
sepsis
severe sepsis and/or
septic shock
*Pneumocystis Carinii* Pnemonia (PCP) as an adjuvant prophylactic or preemptive therapy or as a treatment of PCP manifest ARDS induced by PCP, i.e. before or early in the PCP phase or in manifest ARDS concommitant with the anti-Pneumocystis antibiotic therapy with e.g. Sulfamethoxasol with Trimethoprim.

Pharmaceutical Compositions

Pharmaceutical compositions or formulations for use in the present invention include an TFPI preparation in combination with, preferably dissolved in, a pharmaceutically acceptable carrier, preferably an aqueous carrier or diluent. The pharmaceutical composition may be a solid, a liquid, a gel or an aerosol. A variety of aqueous carriers may be used, such as 0.9% saline, buffered saline, physiologically compatible buffers and the like. The compositions may be sterilized by conventional techniques well known to those skilled in the art. The resulting aqueous solutions may be packaged for use or filtered under aseptic conditions and freeze-dried, the freeze-dried preparation being dissolved in a sterile aqueous solution prior to administration.

The compositions may contain pharmaceutically acceptable auxiliary substances or adjuvants, including, without limitation, pH adjusting and buffering agents and/or tonicity adjusting agents, such as, for example, sodium acetate, sodium lactate, sodium chloride, potassium chloride, calcium chloride, etc. The formulations may contain pharmaceutically acceptable carriers and excipients including microspheres, liposomes, microcapsules, nanoparticles or the like. Conventional liposomes are typically composed of phospholipids (neutral or negatively charged) and/or cholesterol. The liposomes are vesicular structures based on lipid bilayers surrounding aqueous compartments. They can vary in their physiochemical properties such as size, lipid composition, surface charge and number and fluidity of the phospholipids bilayers. The most frequently used lipid for liposome formation are: 1,2-Dilauroyl-sn-Glycero-3-Phosphocholine (DLPC), 1,2-Dimyristoyl-sn-Glycero-3-Phosphocholine (DMPC), 1,2-Dipalmitoyl-sn-Glycero-3-Phosphocholine (DPPC), 1,2-Distearoyl-sn-Glycero-3-Phosphocholine (DSPC), 1,2-Dioleoyl-sn-Glycero-3-Phosphocholine (DOPC), 1,2-Dimyristoyl-sn-Glycero-3-Phosphoethanolamine (DMPE), 1,2-Dipalmitoyl-sn-Glycero-3-Phosphoethanolamine (DPPE), 1,2-Dioleoyl-sn-Glycero-3-Phosphoethanolamine (DOPE), 1,2-Dimyristoyl-sn-Glycero-3-Phosphate (Monosodium Salt) (DMPA), 1,2-Dipalmitoyl-sn-Glycero-3-Phosphate (Monosodium Salt) (DPPA), 1,2-Dioleoyl-sn-Glycero-3-Phosphate (Monosodium Salt) (DOPA), 1,2-Dimyristoyl-sn-Glycero-3-[Phospho-rac-(1-glycerol)] (Sodium Salt) (DMPG), 1,2-Dipalmitoyl-sn-Glycero-3-[Phospho-rac-(1-glycerol)] (Sodium Salt) (DPPG), 1,2-Dioleoyl-sn-Glycero-3-[Phospho-rac-(1-glycerol)] (Sodium Salt) (DOPG), 1,2-Dimyristoyl-sn-Glycero-3-[Phospho-L-Serine](Sodium Salt) (DMPS), 1,2-Dipalmitoyl-sn-Glycero-3-[Phospho-L-Serine) (Sodium Salt) (DPPS), 1,2-Dioleoyl-sn-Glycero-3-[Phospho-L-Serine] (Sodium Salt) (DOPS), 1,2-Dioleoyl-sn-Glycero-3-Phosphoethanolamine-N-(glutaryl) (Sodium Salt) and 1,1',2,2'-Tetramyristoyl Cardiolipin (Ammonium Salt). Formulations composed of DPPC in combination with other lipids or modifiers of liposomes are preferred e.g. in combination with cholesterol and/or phosphatidylcholine.

Long-circulating liposomes are characterized by their ability to extravasate at body sites where the permeability of the vascular wall is increased. The most popular way of producing long-circulating liposomes is to attach hydrophilic polymer polyethylene glycol (PEG) covalently to the outer surface of the liposome. Some of the preferred lipids are: 1,2-Dipalmitoyl-sn-Glycero-3-Phosphoethanolamine-N-[Methoxy(Polyethylene glycol)-2000] (Ammonium Salt), 1,2-Dipalmitoyl-sn-Glycero-3-Phosphoethanolamine-N-[Methoxy(Polyethylene glycol)-5000] (Ammonium Salt), 1,2-Dioleoyl-3-Trimethylammonium-Propane (Chloride Salt) (DOTAP).

Possible lipids applicable for liposomes are supplied by Avanti, Polar Lipids, Inc, Alabaster, Ala. Additionally, the liposome suspension may include lipid-protective agents which protect lipids against free-radical and lipid-peroxidative damage on storage. Lipophilic free-radical quenchers, such as alpha-tocopherol and water-soluble iron-specific chelators, such as ferrioxianine, are preferred.

A variety of methods are available for preparing liposomes, as described in, e.g., Szoka et al., Ann. Rev. Biophys. Bioeng. 9:467 (1980), U.S. Pat. Nos. 4,235,871, 4,501,728 and 4,837,028, all of which are incorporated herein by reference. Another method produces multilamellar vesicles of heterogeneous sizes. In this method, the vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous solution of the targeted drug and the targeting component and allowed to hydrate, typically over a 15-60 minute period with agitation. The size distribution of the resulting multilamellar vesicles can be shifted toward smaller sizes by hydrating the lipids under more vigorous agitation conditions or by adding solubilizing detergents such as deoxycholate.

Micelles are formed by surfactants (molecules that contain a hydrophobic portion and one or more ionic or otherwise strongly hydrophilic groups) in aqueous solution.

Common surfactants well known to one of skill in the art can be used in the micelles of the present invention. Suitable surfactants include sodium laureate, sodium oleate, sodium lauryl sulfate, octaoxyethylene glycol monododecyl ether, octoxynol 9 and PLURONIC F-127 (Wyandotte Chemicals Corp.). Preferred surfactants are nonionic polyoxyethylene and polyoxypropylene detergents compatible with IV injection such as, TWEEN-80, PLURONIC F-68, n-octyl-beta-D-glucopyranoside, and the like. In addition, phospholipids, such as those described for use in the production of liposomes, may also be used for micelle formation.

In some cases, it will be advantageous to include a compound, which promotes delivery of the active substance to its target.

Dosing Regimes

The preparations are administered in a manner compatible with the dosage formulation, and in such amount as will be therapeutically effective. The quantity to be administered depends on the subject to be treated, including, e.g. the weight and age of the subject, the disease to be treated and the stage of disease. Suitable dosage ranges are per kilo body weight normally of the order of several hundred µg active ingredient per administration with a preferred range of from about 0.1 µg to 10000 µg per kilo body weight. Using monomeric forms of the compounds, the suitable dosages are often in the range of from 0.1 µg to 5000 µg per kilo body weight, such as in the range of from about 0.1 µg to 3000 µg per kilo body weight, and especially in the range of from about 0.1 µg to 1000 µg per kilo body weight. Using multimeric forms of the compounds, the suitable dosages are often in the range of from 0.1 µg to 1000 µg per kilo body weight, such as in the range of from about 0.1 µg to 750 µg per kilo body weight, and especially in the range of from about 0.1 µg to 500 µg per kilo body weight such as in the range of from about 0.1 µg to 250 µg per kilo body weight. A preferred dosage would be from about 0.1 to about 5.0 mg, preferably from about 0.3 mg to about 3.0 mg, such as from about 0.5 to about 1.5 mg and especially in the range from 0.8 to 1.0 mg per administration. Administration may be performed once or may be followed by subsequent administrations. The dosage will also depend on the route of administration and will vary with the age, sex and weight of the subject to be treated. A preferred dosage of multimeric forms would be in the interval 1 mg to 70 mg per 70 kilo body weight.

Suitable daily dosage ranges are per kilo body weight per day normally of the order of several hundred µg active ingredient per day with a preferred range of from about 0.1 µg to 10000 µg per kilo body weight per day. Using monomeric forms of the compounds, the suitable dosages are often in the range of from 0.1 µg to 5000 µg per kilo body weight per day, such as in the range of from about 0.1 µg to 3000 µg per kilo body weight per day, and especially in the range of from about 0.1 µg to 1000 µg per kilo body weight per day. Using multimeric forms of the compounds, the suitable dosages are often in the range of from 0.1 µg to 1000 µg per kilo body weight per day, such as in the range of from about 0.1 µg to 750 µg per kilo body weight per day, and especially in the range of from about 0.1 µg to 500 µg per kilo body weight per day, such as in the range of from about 0.1 µg to 250 µg per kilo body weight per day. A preferred dosage would be from about 0.1 to about 100 µg, preferably from about 0.1 µg to about 50 µg, such as from about 0.3 to about 30 µg and especially in the range from 1.0 to 10 µg per kilo body weight per day. Administration may be performed once or may be followed by subsequent administrations. The dosage will also depend on the route of administration and will vary with the age, sex and weight of the subject to be treated. A preferred dosage of multimeric forms would be in the interval 1 mg to 70 mg per 70 kilo body weight per day.

Medical Packaging

The compounds used in the invention may be administered alone or in combination with pharmaceutically acceptable carriers or excipients, in either single or multiple doses. The formulations may conveniently be presented in unit dosage form by methods known to those skilled in the art.

It is preferred that the compounds according to the invention are provided in a kit.

Such a kit typically contains an active compound in dosage forms for administration. A dosage form contains a sufficient amount of active compound such that a desirable effect can be obtained when administered to a subject.

Thus, it is preferred that the medical packaging comprises an amount of dosage units corresponding to the relevant dosage regimen. Accordingly, in one embodiment, the medical packaging comprises a pharmaceutical composition comprising a compound as defined above or a pharmaceutically acceptable salt thereof and pharmaceutically acceptable carriers, vehicles and/or excipients, said packaging comprising from 1 to 7 dosage units, thereby having dosage units for one or more days, or from 7 to 21 dosage units, or multiples thereof, thereby having dosage units for one week of administration or several weeks of administration.

The dosage units can be as defined above. The medical packaging may be in any suitable form for intratracheal, intrabronchial or intraalveolar administration. In a preferred embodiment the packaging is in the form of a vial, ampule, tube, blister pack, cartridge or capsule.

When the medical packaging comprises more than one dosage unit, it is preferred that the medical packaging is provided with a mechanism to adjust each administration to one dosage unit only.

Preferably, a kit contains instructions indicating the use of the dosage form to achieve a desirable affect and the amount of dosage form to be taken over a specified time period. Accordingly, in one embodiment the medical packaging comprises instructions for administering the pharmaceutical composition.

EXAMPLES

Example 1

Protocol for Local Pulmonary Treatment with TFPI Through Bronchoalveolar Lavage (BAL)

I. Patient Group to be Treated:

Patients with ventilator associated pneumonia secondary to bacterial Strep. pneumonia, *Pneumocystis Carinii* pneumonia (PCP) or other types of pneumonia or ARDS secondary to sepsis, Disseminated intravascular coagulation (DIC), trauma, pulmonary aspiration pneumonitis, severe pancreatitis or bleomycin induced ARDS with ongoing treatment with mechanical ventilation, with developement of ARDS with reduced oxygenation capacity as revealed by a reduced $PaO_2$/$FiO_2$ ratio, i.e. <200 mmHg (arterial oxygen tension in mmHg over inspired oxygen fraction) in spite of treatment with full antibiotic coverage towards the isolated microbiological agent or treatment of underlying disease.

II. Treatment Regime:

Local administration of 5 mg TFPI dissolved in 20 ml of normal saline via Bronchoalveolar lavage (BAL).

III. Analysis of Results:

a) Monitoring of oxygenation capacity as by monitoring the PaO2/FiO2 ratio (arterial oxygen tension in mmHg over inspired oxygen fraction). A successful treatment results in an increase in oxygen capacity with a $PaO_2$/$FiO_2$ ratio, i.e. >200 mmHg.

b) Radiography of the lung field before and after treatment. As the patients have infiltrations in the lung a successful treatment leads to reduction of these infiltrations as monitored by radiography.

Example 2

Protocol for Local Pulmonary Treatment with TFPI Through Inhalation

I. Patient Group to be Treated:

Patients with ventilator associated pneumonia secondary to bacterial Strep. Pneumonia, *Pneumocystis Carinii* pneumonia or other types of pneumonia or ARDS secondary to sepsis, Disseminated intravascular coagulation (DIC), trauma or pulmonary aspiration pneumonitis or severe pancreatitis or or bleomycin induced ARDS with ongoing treatment with mechanical ventilation, with developement of ARDS with reduced oxygenation capacity as revealed by a reduced $PaO_2$/$FiO_2$ ratio, i.e. <200 mmHg (arterial oxygen tension in mmHg over inspired oxygen fraction) in spite of treatment with full antibiotic coverage towards the isolated microbiological agent or treatment of underlying disease.

II. Treatment Regime:

Local administration of 3×5 mg TFPI via a nebulizer (Aeroneb®).

III. Analysis of Results:

a) Monitoring of oxygenation capacity as by monitoring the $PaO_2/FiO_2$ ratio (arterial oxygen tension in mmHg over inspired oxygen fraction). A successful treatment results in an increase in oxygen capacity with a $PaO_2/FiO_2$ ratio, i.e. >200 mmHg.

b) Radiography of the lung field before and after treatment. As the patients have infiltrations in the lung a successful treatment leads to reduction of these infiltrations as monitored by radiography.

The invention claimed is:

1. A method for treating or reducing risk of extravascular fibrin deposition in the airways, in particular the alveolar or bronchoalveolar spaces, in a human subject comprising administering to the subject human tissue factor pathway inhibitor (TFPI) or a biologically active TFPI homologue having a sequence identity of greater than 85% to TFPI as the only active ingredient, via the airway by means of intratracheal, intrabronchial or intraalveolar administration.

2. The method of claim 1, wherein the fibrin deposition is caused by an inflammatory lung disease.

3. The method of claim 2, wherein the inflammatory lung disease is selected from the group consisting of acute lung injury (ALI), acute respiratory distress syndrome (ARDS), pneumonia, acute bronchoalveolar diseases, chronic bronchoalveolar diseases, fibrosing alveolitis and bronchial asthma.

4. The method of claim 2, wherein the inflammatory lung disease is related to a condition selected from the group consisting of direct or indirect pulmonary trauma, pancreatitis, aspiration pneumonitis, sepsis, severe sepsis, septic shock and drug induced acute lung insufficiency.

5. The method of claim 1, wherein the tissue factor pathway inhibitor is administered by bronchoalveolar lavage with a solution of the tissue factor pathway inhibitor.

6. The method of claim 1, wherein the tissue factor pathway inhibitor is administered by blind tracheal washing with a solution of the tissue factor pathway inhibitor.

7. The method of claim 1, wherein the tissue factor pathway inhibitor is administered by causing the inhalation of a nebulized solution of the tissue factor pathway inhibitor.

8. The method of claim 1, wherein the tissue factor pathway inhibitor is administered by causing the inhalation of the tissue factor pathway inhibitor in inhaled powder form.

9. The method of claim 1, wherein the tissue factor pathway inhibitor is administered by direct application of the tissue factor pathway inhibitor during bronchoscopy.

10. The method of claim 1 wherein the human subject is an adult.

11. The method of claim 1 wherein the human subject is a child.

12. The method of claim 1, wherein the TFPI is administered in an amount of from 0.1 µg/kg to about 10 mg/kg body weight per day.

13. The method of claim 1 wherein the TFPI homologue has a sequence identity of greater than 90% to TFPI.

* * * * *